US005871728A

United States Patent [19]
Thomson et al.

[11] Patent Number: 5,871,728
[45] Date of Patent: Feb. 16, 1999

[54] METHOD OF REGULATING DENDRITIC CELL MATURATION

[75] Inventors: Angus W. Thomson, Pittsburgh; Anthony J. Demetris, Glenshaw; Thomas E. Starzl, Pittsburgh, all of Pa.

[73] Assignee: University of Pittsburgh, Pittsburgh, Pa.

[21] Appl. No.: 414,461

[22] Filed: Mar. 31, 1995

[51] Int. Cl.[6] .................................................. C12N 5/08
[52] U.S. Cl. ........................................... 424/93.7; 604/93
[58] Field of Search ..................................... 424/93.7, 550, 424/529, 553, 578, 572, 184.1, 1.49, 152.1, 810; 435/240.1, 240.2; 530/412; 604/93

[56] References Cited

PUBLICATIONS

Lu et al., Immunology, "Generation of DC from mouse spleen cell cultures in response to GM–CSF: immunophenotypic and functional analyses," 84:127–134 (1995).
Paglia et al., J. Exp. Med., "Immortalized Dendritic Cell Line Fully Competent in Antigen Presentation Initiates Primary T Cell Responses In Vivo," 178:1893–1901 (1993).
Starzl et al., Prog. Liver Dis., "Migratory Nonparenchymal Cells After Organ Allotransplantation: With Particular Reference to Chimerism and the Liver," 12:191–213 (1994).
Thomson et al., Transplantation Proceedings, "Propagation of Dendritic Cell Progenitors From Mouse Liver and Their In Vivo Migration to T–Dependent Areas of Allogeneic Lymphoid Tissue," 26:4084–4086 (1994).
Thomson, et al., Dendritic Cells in Fundamental and Clinical Immunology, vol. 2 (Banchereau, J. and D. Schmitt, ed.) "Exposure to Type–I Collagen Induces Maturation of Mouse Liver Dendritic Cell Progenitors," pp. 511–518 (1995).
Qian, et al., Hepatology, "Murine Liver Allograft Transplantation: Tolerance and Donor Cell Chimerism," 19:916–924 (1994).
Starzl, et al., Lancet, "Cell migration, chimerism, and graft acceptance," 339:1579–1582 (1992).
Starzl, et al., Immunol. Today, "Donor cell chimerism permitted by immunosuppressive drugs: a new view of . . . " 14:326–332 (1993).
Starzl, et al., Hepatology, "Cell Migration and Chimerism After Whole–Organ Transplation . . . " 17:1127–1152 (1993).
Steinman, et al., Hepatology, "Donor–derived Chimerism in Recipients . . . ", 17:1153–1156 (1993).
Demetris, et al., Transplant. Proc., "Hematolymphoid Cell Trafficking, Microchimerism, and GVH . . . ," 25:3337–3344 (1993).
Yoshimura, et al., Transplantation, "The Effects of Perioperative Portal Venous Inoculation . . . ," 49:167–171 (1990).
Thomas, et al., Transplantation, "Kidney Allograft Tolerance in Primates . . . ", 51:198–207 (1991).
Van Twuyver, et al., N. Engl. J. Med., "Pretransplantation Blood Transfusion Revisited . . . ," 325:1210–1213 (1991).
Barber, et al., Transplantation, "Long–Term Results of a Controlled Prospective Study with Transfusion . . . ," 51:70–75 (1991).

Murphy, et al., Proc. Natl. Acad. Sci. USA, "Peripheral tolerance to allogeneic class II . . . ," 86:10034–10038 (1989).
Miller et al., Annu. Rev. Immunol., "Peripheral T Cell Tolerance," 10:51–69 (1992).
Thomas, et al., Transplantation, "Further Studies of Veto Activity in Rhesus Monkey . . . ," 57:101–115 (1994).
Streilein, et al., J. Neuroimmunol., "Immunoregulatory mechanisms of the eye," 39:185–200 (1992).
Wilbanks, et al., J. Immunol., "Studies on the Induction of Anterior . . . ," 146:2610–2617 (1991).
Wilbanks, et al., J. Immunol., "Studies on the Induction of Anterior . . . ," 146:3018–3024 (1991).
Starzl, et al., Surgery, "Factors determining short and long–term . . . ," 58:131–155 (1965).
Calne, et al., Nature, "Induction of Immunological Tolerance by Porcine . . . ," 223:472–476 (1969).
Hart, et al., J. Exp. Med., "Demonstration and Characterization of Ia–Positive Dendritic . . . ," 154:347–361 (1981).
Steiniger, et al., Transplantation, "Phenotype and Histological Distribution of Interstitial . . . ," 38:169–175 (1984).
Prickett, et al., Transplantation, "Characterization of Interstitial Dendritic . . . ," 46:754–761 (1988).
Inaba, et al., J. Exp. Med., "Indentification of Proliferating Dendritic . . . ," 175:1157–1167 (1992).
Inaba, et al., J. Exp. Med., "Generation of Large Numbers of Dendritic Cells . . . ," 176:1693–1702 (1992).
Martinez–Hernandez, Lab. Invest., "The Hepatic Extracellular Matrix," 51:57–74 (1984).
Lu, et al., J. Exp. Med., "Propagation of Dendritic Cell Progenitors . . . ," 179:1823–1834 (1994).
Woo, et al., Transplantation, "Isolation, Phenotype, and Allostimulatory . . . ," 58:484–491 (1994).
Starzl, et al., Immunological Reviews, "The Biological Basis of Strategies for Clinical Xenotransplantation," 141:213–244 (1994).

(List continued on next page.)

*Primary Examiner*—Jean C. Witz
*Attorney, Agent, or Firm*—Cushman, Darby & Cushman IP Group of Pillsbury Madison & Sutro

[57] ABSTRACT

A novel transplantation method for enhancing tolerogenicity in a host mammal to a transplant graft specimen from a donor mammal is disclosed. According to this method, immature mammalian dendritic cells propagated in the presence of a cytokine are administered to the host mammal in advance of transplantation. Tolerogenicity is enhanced in the host mammal when the immature mammalian dendritic cells concentrate in T-dependent regions of secondary lymphoid tissue of the host mammal, where the expression of major histocompatibility complex class II antigen by the immature mammalian dendritic cells is upregulated. Also disclosed is a novel method of effecting the maturation of immature dendritic cells in the presence of a cytokine and an extracellular matrix protein. These mature mammalian dendritic cells, which upregulate the expression of major histocompatibility complex class II antigen, can then be used to enhance the immune response of a host mammal.

75 Claims, 8 Drawing Sheets

PUBLICATIONS

Steinman, et al., J. Exp. Med., "Identification of a Novel Cell Type . . . ," 137:1142–1162 (1973).

Steinman, et al., J. Exp. Med., "Identification of a Novel Cell Type in Peripheral . . . ," 139:380–397 (1973).

Larsen, et al., J. Exp. Med., "Migration of Dendritic Leukocytes from Cardiac . . . ," 171:307–314 (1990).

Larsen, et al., J. Exp. Med., "Migration and Maturation of Langerhans Cells . . . ," 172:1483–1493 (1990).

Thomson, et al., Transplantation, "In Vitro Propagation and Homing of Liver–Derived Dendritic . . . ," 59:1–7 (1995).

METHOD OF REGULATING DENDRITIC CELL MATURATION

FIELD OF THE INVENTION

The present invention relates to the propagation of immature mammalian dendritic cells (DC) and uses thereof, including improvements in the tolerogenicity in a host mammal of a graft specimen transplanted from a donor mammal. The present invention further relates to the maturation of mammalian DC and uses thereof, including the enhancement of a mammal's immune response.

BACKGROUND OF THE INVENTION

Murine studies have demonstrated that liver grafts can survive permanently when transplanted into hosts that have not been immunologically suppressed (Qian, et al., Hepatology, 19:916 (1994)). Similarly, these transplanted liver grafts have also been shown to induce donor-specific acceptance of skin and cardiac grafts (Qian, et al., Hepatology, 19:916 (1994)). The inventors believe that such graft acceptance in a host depends on the presence of bone marrow-derived leukocytes in the transplanted specimen (Starzl, et al., Lancet, 339:1579 (1992); Starzl, et al., Immunol. Today, 14:326 (1993); Starzl, et al., Hepatology, 17:1127 (1993)).

Following transplantation, the migration of bone-marrow derived cells from whole organs appears to result in a low level chimerism and donor-specific immunological non-reactivity (Starzl, et al., Lancet, 339:1579 (1992); Starzl, et al., Immunol. Today, 14:326 (1993); Qian, et al., Hepatology, 19:916 (1994)). The inventors believe that cell migration and chimerism may be the basis for acceptance of all allografts (Starzl, et al., Lancet, 339:1579 (1992); Starzl, et al., Immunol. Today, 14:326 (1993); Starzl, et al., Hepatology, 17:1127 (1993)). Thus, the exceptional tolerogenicity of the liver could mirror a comparatively heavy content of immature or progenitor DC within this organ (Steinman, et al., Hepatology, 17:1153 (1993)).

Additional studies by the inventors have shown that the propagation of myeloid lineage cells from normal mouse heart non-parenchymal cells (NPC) in the presence of granulocyte-macrophage colony stimulating factor (GM-CSF) is difficult to achieve. The possibility that multiple hematolymphopoietic lineages participate in the leukocyte traffic occurring after an organ transplant has been suggested from observations in rats (Demetris, et al., Transplant. Proc., 25:3337 (1993)) and humans (Starzl, et al., Hepatology, 17:1127 (1993)), and demonstrated unequivocally in mouse liver transplant experiments (Qian, et al., Hepatology, 19:916 (1994)). These lineages may survive permanently without treatment in mice (Qian, et al., Hepatology, 19:916 (1994)) or subsequent to an immunosuppressive regimen in rats (Demetris, et al., Transplant. Proc., 25:3337 (1993)) and, in some cases, humans (Starzl, et al., Hepatology, 17:1127 (1993)). The probability of pluripotent stem cells and immature DC—amongst other lineages—in the bone marrow-derived interstitial population of non-lymphoid organs is inherent in the inventors' cell migration and chimerism explanation (Starzl, et al., Lancet, 339:1579 (1992); Starzl, et al., Immunol. Today, 14:326 (1993)).

Once a graft specimen has been transplanted, the bone marrow-derived leukocytes, otherwise known as "passenger leukocytes," migrate from the donor specimen into the host's tissue (Starzl, et al., Lancet, 339:1579 (1993); Starzl, et al., Immunol. Today, 14:326 (1993)). Once in the host's tissue, evidence exists that a complex of interactions between the donor's leukocytes and the host's immune system can lead to a decreased immune response in the host, and even to tolerance induction in certain situations (Starzl, et al., Lancet, 339:1579 (1993); Starzl, et al., Immunol. Today, 14:326 (1993); Demetris, et al., Transplant. Proc., 25:3337 (1993); Starzl, et al., Hepatology, 17:1127 (1993); Yoshimura, et al., Transplantation, 49:167 (1990); Thomas, et al., Transplantation, 51:198 (1991); Van Twuyver, et al., N. Engl. J. Med., 325:1210 (1991); Barber, et al., Transplantation, 51:70 (1991)). Numerous reports also exist indicating that mature T-cells can be tolerized to allogeneic antigens outside the thymus (Murphy, et al., Proc. Natl. Acad. Sci. U.S.A., 86:10034 (1989); Miller, et al., Annu. Rev. Immunol., 10:51 (1992)). Accordingly, chimeric cells present in the periphery may play a key role in achieving allotolerance.

HLA-DR$^{dim}$ allogeneic donor bone marrow cells showing veto cell activity—inactivation of T-helper cells or cytotoxic T-cell precursors—have also been postulated to be immature DC (Thomas, et al., Transplantation, 57:101 (1994)). These immature DC were shown by the present inventors to have avid phagocytic activity in culture and might be expected, therefore, to elicit a deviant, or tolerogenic, local and systemic immune response shortly after injection thereof. The precise basis of the DC-T-cell interaction leading to tolerance induction is not known at this time. Nonetheless, such an interaction would logically depend on the relative affinity or avidity of the donor DC-T-cell receptors ("TCR"), and on the expression of adhesions and co-stimulatory molecules (e.g., B7-1 and B7-2) on the former cells.

An example of a thoroughly studied atypical or "deviant" cytokine-modulated immune response induced by bone marrow-derived antigen-presenting cells ("APC") is provided by Streilein et al. (Streilein, et al., J. Neuroimmunol., 39:185 (1992); Wilbanks, et al., J. Immunol., 146:2610 (1991)). Streilein and his colleagues studied class II$^{dim}$ APC with dendritic morphology, which are now believed to be variant DC in the iris, ciliary body, and other tissues lining the anterior chamber of the eye (Wilbanks, et al., J. Immunol., 146:3018 (1991); Streilein, et al., J. Neuroimmunol., 39:185 (1992)). After APC took up bovine serum albumin ("BSA") injected into the anterior chamber of test specimens, the BSA was presented ineffectively to local T-cells, and subsequently in the spleen when APC-peptide complexes arrived there. As a consequence, the test specimen experienced both a dampened systemic and local, or ocular, immune response when challenged with antigen. Although DC precursors appear to be concentrated in the liver, similar subpopulations presumably exist in all other tissues and whole organs, and particularly in the bone marrow, which constitutes a major source of leukocytes.

The liver, which is the most tolerogenic whole organ (Starzl, et al., Hepatology, 17:1127 (1993); Starzl, et al., Surgery, 58:131 (1965);

Calne, et al., Nature, 223:472 (1969)), possesses a relatively large concentration of DC. And across most mouse strain combinations, a liver can be transplanted without host immunosuppression (Qian, et al., Hepatology, 19:916 (1994)). Although interstitial liver DC have been characterized by immunohistochemical studies in both rodents (Hart, et al., J. Exp. Med., 154:347 (1981); Steiniger, et al., Transplantation, 38:169 (1984)) and humans (Prickett, et al., Transplantation, 46:754 (1988)), there is a dearth of published data concerning the in vitro properties of liver DC, and there have been no known attempts to propagate DC from a normal liver.

Reports indicate that the destination of the passenger leukocytes after whole organ transplant is lineage-specific, following the same routes taken by syngeneic cells of the same lineages (Demetris, et al., Transplant. Proc., 25:3337 (1993); Qian, et al., Hepatology, 19:916 (1994)). Moreover, the bone marrow-derived DC lineage is postulated to be the most important of the passenger leukocytes, providing variable degrees of donor-specific non-reactivity (Starzl, et al., Lancet, 339:1579 (1993); Starzl, et al., Immunol. Today, 14:326 (1993); Demetris, et al., Transplant. Proc., 25:3337 (1993)).

Although it has previously been postulated that complex interactions between donor leukocytes and a host's immune system may lead to a decreased immune response by the host (Starzl, et al., Lancet, 339:1579 (1993); Starzl, et al., Immunol. Today, 14:326 (1993); Demetris, et al., Transplant. Proc., 25:3337 (1993); Starzl, et al., Hepatology, 17:1127 (1993); Yoshimura, et al., Transplantation, 49:167 (1990); Thomas, et al., Transplantation, 51:198 (1991); Van Twuyver, et al., N. Engl. J. Med., 325:1210 (1991); Barber, et al., Transplantation, 51:70 (1991)), and even to tolerance induction, reports of attempts to propagate DC lineage cells from a normal liver are not known to exist.

And despite the fact that DC progeny from mouse blood and bone marrow have been propagated and matured in the presence of GM-CSF (Inaba, et al., J. Exp. Med., 175:1157 (1992); Inaba, et al., J. Exp. Med., 176:1693 (1992)), attempts by the inventors to culture liver-derived DC in the presence of a cytokine alone, such as GM-CSF, failed to achieve appreciable differentiation of liver DC in vitro. The additional presence of tumor necrosis factor-$\alpha$ ("TNF-$\alpha$") and/or interferon-$\gamma$ ("INF-$\gamma$") was likewise found by the inventors to be ineffective in raising the level of major histocompatibility complex ("MHC") class II expression in mouse-derived liver DC. Prior to the present invention, no known means existed for maturing DC derived from an hepatic source.

The present invention provides a method of propagating immature or undifferentiated mammalian DC in the presence of a cytokine, which may then be used to induce donor-specific tolerance to grafts transplanted to a host mammal. The present invention further provides a method of producing immunologically mature mammalian DC in the presence of a cytokine and an extracellular matrix protein, which may then be used to enhance the immune response, including antibody production and cell-mediated immunity, of a host mammal.

SUMMARY OF THE INVENTION

The present invention relates to a method of propagating immature mammalian DC which are effective in enhancing tolerogenicity to a foreign graft specimen comprising the steps:

(a) isolating immature dendritic cells from a mammalian source; and (b) propagating said immature dendritic cells in the presence of a cytokine, wherein said cells are effective in enhancing tolerogenicity,.

In another embodiment, the present invention relates to a composition containing immature mammalian DC, which composition is suitable for increasing the tolerogenicity in a host mammal of a foreign graft specimen.

In a further embodiment, the present invention relates to a kit for enhancing the tolerogenicity of a host mammal to a foreign graft specimen from a donor mammal, which kit contains immature mammalian DC.

In an additional embodiment, the present invention relates to a protocol for increasing the tolerogenicity in a host mammal to a foreign graft specimen comprising:

(a) isolating immature mammalian DC from a donor mammal;

(b) propagating the immature mammalian DC in the presence of a cytokine; and (c) administering the propagated immature mammalian DC in a tolerogenicity enhancing amount to the host mammal.

In yet another embodiment, the present invention also relates to a surgical transplant procedure for increasing graft acceptance in a host mammal comprising:

(a) administering to a host mammal immature mammalian DC, and (b) transplanting to the host mammal a graft specimen derived from the donor mammal.

The present invention also relates to a method for producing immunologically mature mammalian DC, whereby immature mammalian DC are cultured in the presence of a cytokine and an extracellular matrix protein.

In another embodiment, the present invention relates to a composition having mature mammalian DC, which composition is suitable for enhancing the immune response of a host mammal.

In a further embodiment, the present invention relates to a kit for enhancing the immune response of a host mammal, which kit contains mature mammalian DC.

In an additional embodiment, the present invention relates to a method of enhancing the immune response of a host mammal comprising:

(a) isolating immature mammalian DC from a donor mammal;

(b) maturing said immature mammalian DC in the presence of a cytokine and an extracellular matrix protein; and (c) administering said mature mammalian DC to said host mammal in an amount effective to enhance the immune response of said host mammal.

These and other features, aspects and advantages of the present invention will become better understood with reference to the following description and appended claims.

DETAILED DESCRIPTION OF THE INVENTION

Figure 1:
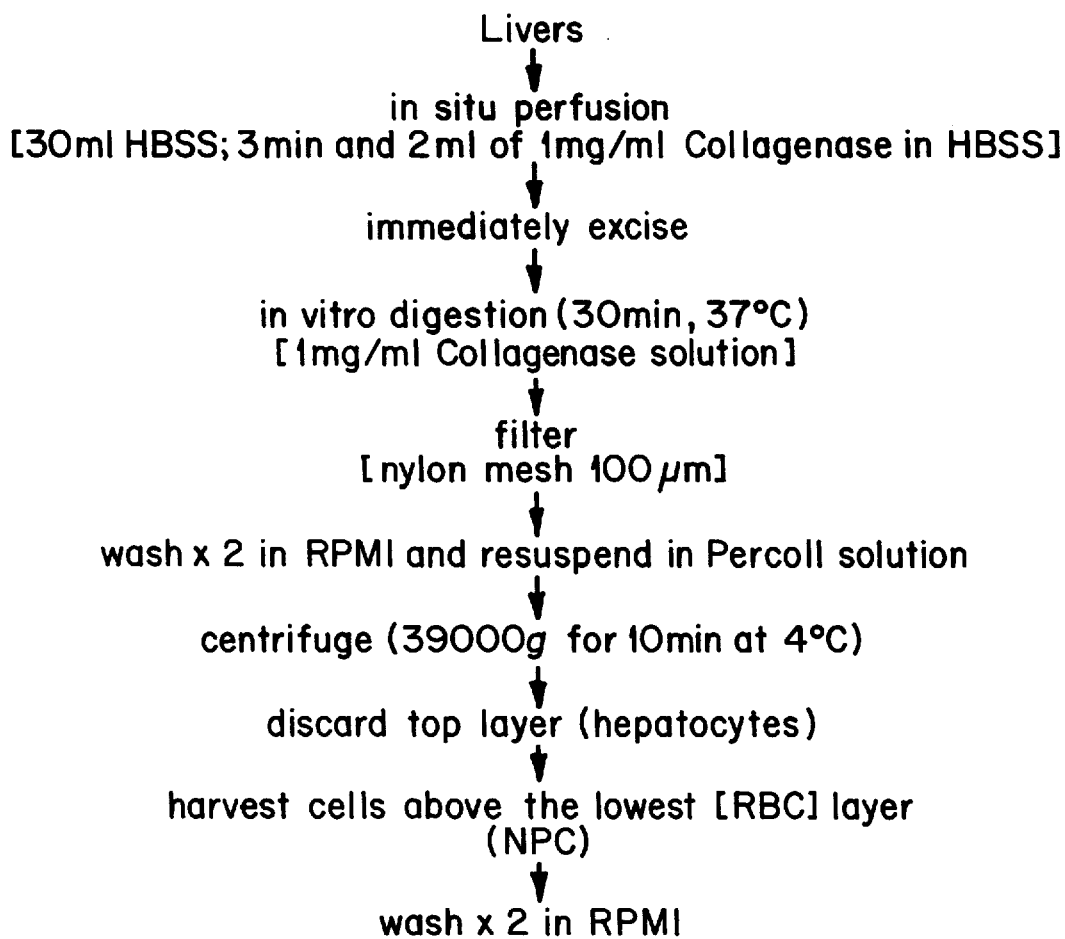
FIG. 1. This figure shows the flow plan for a method of isolating NPC from a mammalian liver. These NPC can then be cultured in accordance with the methods of the present invention to propagate or effect maturation of immature mammalian DC.
Figure 2A:
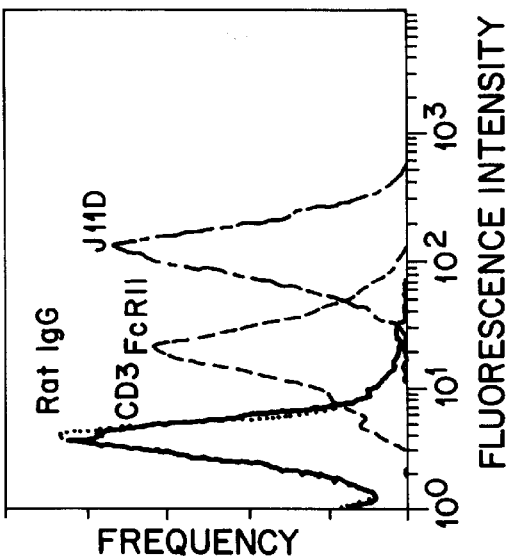
FIGS. 2A to 2F. These figures shows merged FACScan® immunophenotypic profiles of the GM-CSF-stimulated liver-derived putative DC released from cell aggregates 10 days after cultures were initiated. The cultures were examined using rat, hamster or mouse mAbs. Details of these mAbs are provided in Table 1. All data were obtained from the same cell preparation. The data represent the results of 4 separate experiments performed using cells attained from 6–10 day cultures. The profile of this figure is consistent with an immature DC phenotype.
Figure 2B:
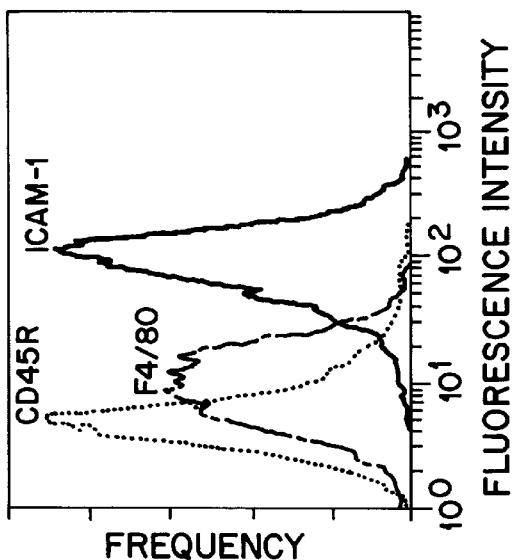
Figure 2C:
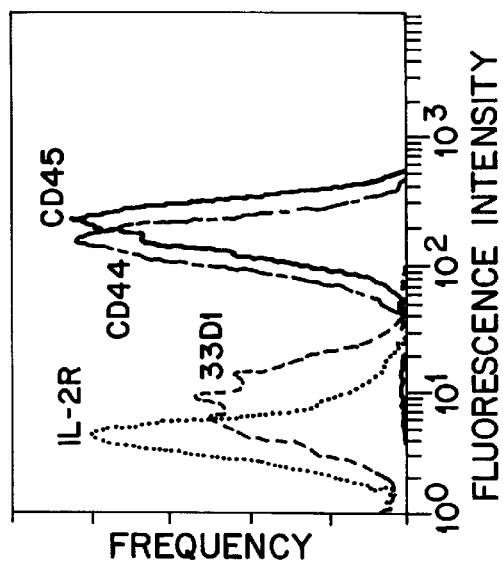
Figure 2D:
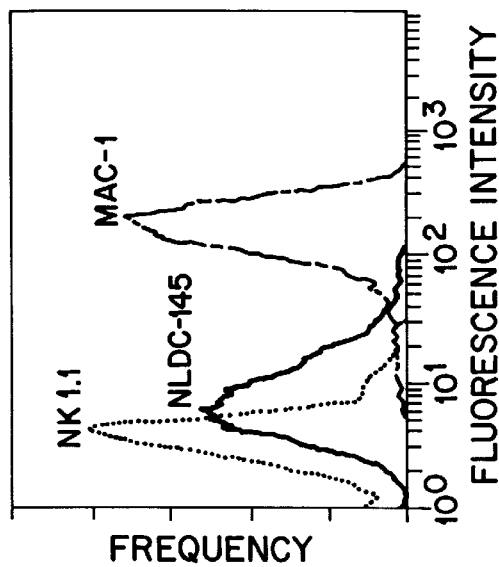
Figure 2F:
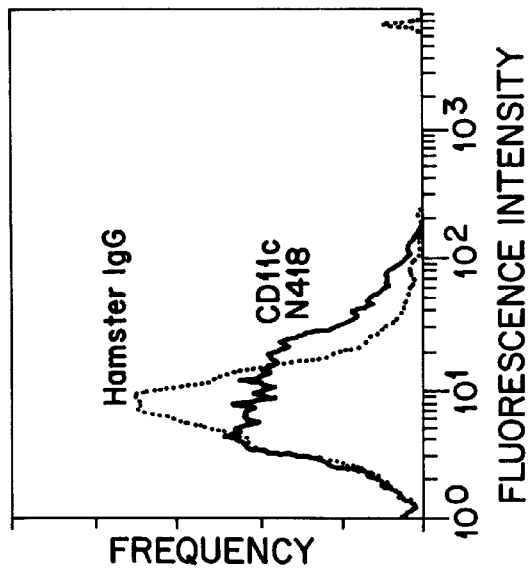
Figure 2E:
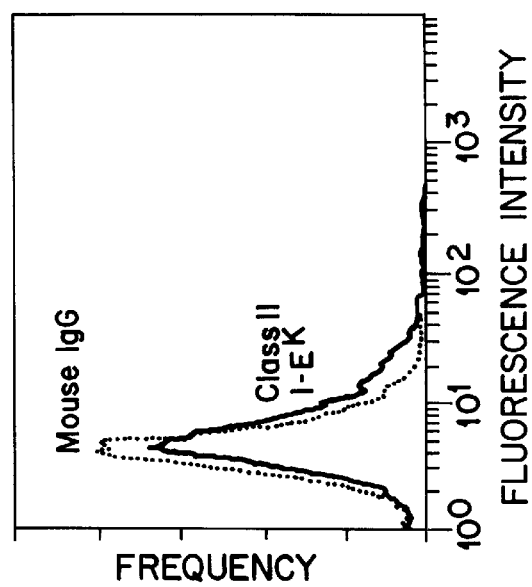
Figure 3:
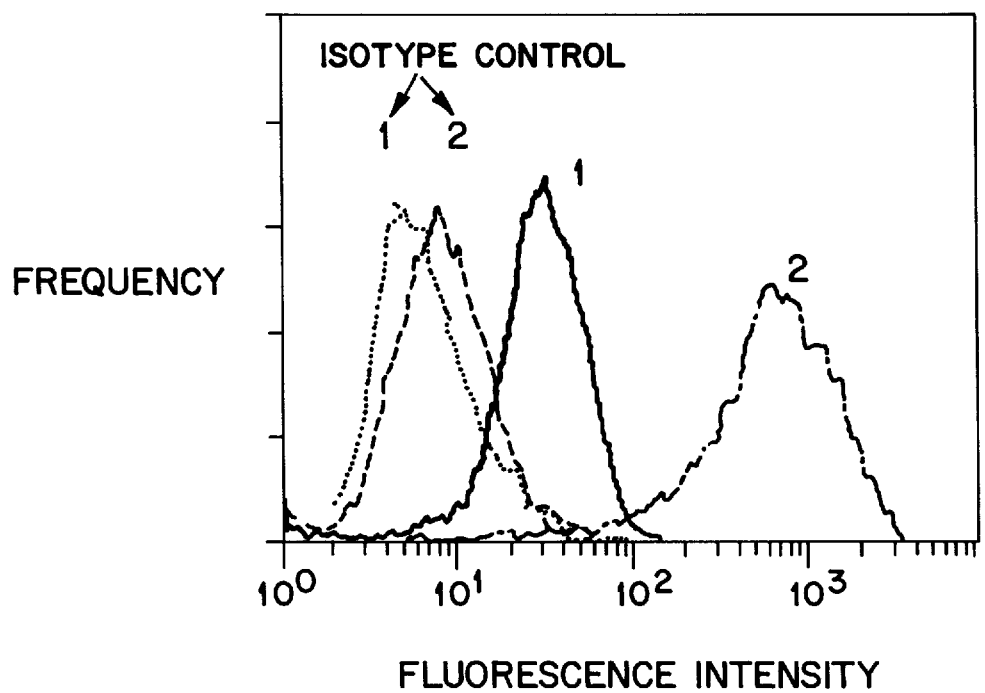
FIG. 3. This figure shows a cytometric analysis of MHC class II (I-E$^k$) expression on GM-CSF-stimulated mouse liver putative DC (1) and spleen-derived DC released from proliferating aggregates in 10 day cultures (2). The data represent the results of 6 separate experiments performed using cells obtained from 6–10 day cultures. The liver-derived GM-CSF-stimulated cells expressed only a low level of MHC class II (I-E$^k$) surface antigen molecule when compared to GM-CSF-stimulated spleen cells propagated under the same conditions.

The present invention is based in part on the discovery that immature mammalian DC have an apparent ability to enhance tolerance in a host mammal to a foreign graft specimen from a donor mammal, thereby increasing the likelihood of graft acceptance in the host mammal. A foreign graft specimen in the present invention is defined to be a graft specimen from a source other than the host mammal. A donor mammal is defined in the present invention to be the source of a graft specimen for transplantation to another mammal. A host mammal is defined in the present invention to be the recipient of a graft specimen from a donor mammal, where the donor mammal and the host mammal are distinct entities. The graft specimens of the present invention can be either homografts or xenografts, where a homograft is a graft specimen transplanted between mammals of the same species and a xenograft is a graft specimen transplanted between mammals of different species. The graft material of the present invention can be taken from, for example, an organ, tissue, bone marrow or blood.

Tolerogenicity of graft specimens according to the present invention is positively affected because the immature DC from the donor mammal selectively home to T-dependent areas of secondary lymphoid tissue in the host mammal, whereupon they upregulate their expression of MHC class II surface antigen. These surface antigens then act to influence the immune response of the host, and may induce tolerance in the host. The inventors believe that the expression of donor MHC class II can, without the expression of critical co-stimulatory molecules, such as, for example, B7-1 and B7-2, induce tolerance in a host mammal to a donor graft specimen, as opposed to immune reactivity.

The present invention is also predicated on the discovery that immature DC from a mammalian source may be induced to differentiate in the combined presence of a cytokine and an extracellular matrix protein. Specifically, the cytokine and extracellular matrix protein combination of the present invention has been shown to induce differentiation of immature DC from a mammalian liver. Additional sources of immature mammalian DC envisaged by the present invention include, for example, other organs, tissue, bone marrow and blood.

When cultured in the presence of a cytokine alone, liver-derived DC are not known to differentiate to any significant degree. This failure to differentiate is demonstrated by the absence or weak expression of MHC class II antigen and a failure to stimulate allogeneic T-cells, which typically provide evidence that DC have matured.

It was shown by the inventors that when immature liver-derived DC are exposed to a cytokine in combination with an extracellular matrix protein, such DC manifest physiological signs of differentiation. These signs of differentiation include an upregulated expression of MHC class II antigen, a reduction in phagocytic capacity and the acquisition of potent allostimulatory activity.

The possibility that these manifestations of differentiation could be attributable to the selective enrichment of Ia$^{dim}$ cells after exposure to collagen, rather than to the functional and phenotypic maturation of liver-derived DC precursors, was precluded by showing that when Ia$^-$, GM-CSF-propagated liver-derived DC are exposed to collagen, they mature into potent antigen-presenting cells expressing equally high levels of MHC class II antigen.

The inventors determined that culturing liver-derived NPC cells in the presence of GM-CSF and type-1 collagen creates an environment similar to that of the microenvironment of the intact liver, where mature DC are typically concentrated. Those regions of the liver possessing significant populations of mature DC have also been found to be rich in type-1 collagen and include the portal tracts and areas around central veins and in Glisson's capsule (Martinez-Hernandez, Lab. Invest., 51:57 (1984)).

In one embodiment, the present invention relates to a method of propagating immature mammalian DC which are effective in enhancing tolerogenicity to a foreign graft specimen, whereby immature mammalian DC are propagated in the presence of a cytokine using conventional culturing techniques. An example of such conventional culturing techniques is detailed in the Examples section hereinbelow. Similar culturing techniques are also described in Lu, et al., J. Exp. Med., 179:1823 (1994), the contents of which are herein incorporated by reference. Additionally, skilled practitioners would appreciate modifications that could be made to the disclosed culturing techniques without engaging in undue experimentation.

Mammalian liver and bone marrow are the preferred sources of immature DC for propagation in the presence of a cytokine. Examples of cytokines that may be used in the present invention, alone or in any combination, include, but are not limited to, GM-CSF, interleukin-1 ("IL-1"), interleukin-4 ("IL-4") and tumor necrosis factor-$\alpha$ ("TNF-$\alpha$"). The cytokine is preferably GM-CSF.

In another embodiment, the present invention relates to a composition containing immature mammalian DC, which is useful for enhancing tolerogenicity in a host mammal to a foreign graft specimen. Increased tolerogenicity is evidenced by a homing of the DC to T-dependent areas of secondary lymphoid tissue in the host mammal, where the DC upregulate their expression of MHC class II surface antigen. The immature mammalian DC are preferably propagated in accordance with the method of propagation described hereinabove.

In a further embodiment, the present invention relates to a method of enhancing the tolerogenicity in a host mammal to a foreign graft specimen comprising:

(a) isolating immature mammalian DC from a donor mammal;

(b) propagating the immature mammalian DC from the donor mammal in the presence of a cytokine; and (c) administering said propagated immature mammalian DC in a tolerogenicity enhancing amount to the host mammal.

Isolating immature mammalian DC may be accomplished in accordance with the method described in the Examples section hereinbelow. A similar method for isolating DC is also described in Woo et al., Transplantation, 58:484 (1994), the contents of which are herein incorporated by reference. Those skilled in the art would be able to implement modifications to the disclosed method of isolating immature mammalian DC without the exercise of undue experimentation.

Once isolated, the immature mammalian DC are preferably propagated in accordance with the method described in the Examples section hereinbelow. Means of administering the propagated DC include, but are not limited to, intravenous, subcutaneous and intraperitoneal administration. The propagated DC are preferably administered intravenously.

Administering a single dose in the range of 1-to-$2 \times 10^6$ immature DC to a mouse was found by the inventors to significantly prolong graft survival. More particularly, the intravenous administration of $2 \times 10^6$ immature DC to mice was discovered to significantly increase allograft survival rates. (Thomson, et al., In Press (1995)). To achieve maximum survival, multiple injections may be required.

Prophylactic administration of immature mammalian DC may be instituted prior to transplantation. More particularly, the prophylactic administration of immature mammalian DC may be commenced approximately one week before transplantation. A purpose of administering immature mammalian DC prior to transplantation is to adapt the host system to the graft specimen.

Immature mammalian DC may also be administered at the time of transplantation and up to about one week after administration. Practitioners may also continue to administer immature DC at subsequent intervals over an indefinite period of time in order to ensure optimum graft acceptance.

The inventors' composition and method of enhancing tolerogenicity may also include the addition of one or more immunosuppressive agents in dosage unit form. Examples of immunosuppressive agents that can be used in the inventors' method of enhancing tolerogenicity include, but are not limited to, cytokines such as, for example, interleukin-10 ("IL-10") and transforming growth factor-$\beta$ ("TGF-$\beta$"), and pharmaceuticals such as, for example, cyclosporine A and tacrolimus (FK 506).

Immunosuppressive agents are typically administered to a host mammal at the time of graft transplantation and daily thereafter for a period of time necessary to optimize graft survival. Practitioners will know to adjust the amount of any immunosuppressive agent administered based upon its potency and potential toxicity. The amount of immunosuppressive agents employed will also vary depending upon such factors as the efficacy of immature mammalian DC administered to the host, the presence or absence of infection or malignant disease in the host, as well as the unique response of the host to the presence of a particular graft specimen.

Examples of dosage unit forms contemplated by the present invention include capsule, tablet and emulsion for per os administration and a solution for intravenous, subcutaneous and intramuscular administration. Intravenous administration is preferred.

A pharmaceutically acceptable carrier may also be used with the present composition and method of enhancing tolerogenicity. Pharmaceutically acceptable carriers within the purview of the present invention include, but are not limited to, olive oil/ethanol and hydroxypropyl methyl cellulose (solid dispersion) for per os administration of cyclosporine, and cremophor (polyoxyethylated sulphonated caster oil derivative) for intravenous administration of cyclosporine. Similar pharmaceutical carriers can be used with tacrolimus (FK 506).

To determine appropriate times for administering of immature mammalian DC, skilled artisans will need to employ conventional clinical and laboratory means for monitoring graft survival, graft function and a host's reactivity to a transplant. Such means include known biochemical and immunological tests for monitoring and assessing host acceptance of a transplanted graft specimen.

In yet a further embodiment, the present invention relates to a kit for use in increasing the tolerogenicity in a host mammal to a foreign graft specimen from a donor mammal, which kit contains immature mammalian DC, such as the composition described hereinabove. The immature mammalian DC may be isolated in accordance with methods described hereinabove, and are preferably stored in a lyophilized form. The kit of the present invention may additionally contain a regimen of one or more immunosuppressive agents and a pharmaceutically acceptable carrier, as described hereinabove.

It is not necessary that the immature mammalian DC be isolated from the same source as the graft specimen to be transplanted, provided the immature mammalian DC and the graft specimen are histocompatible. Determining the histocompatibility between immature DC and a graft specimen can be accomplished using conventional tissue typing procedures that identify MHC gene products that are expressed on the surfaces of the immature DC and cells of the host.

The kit may also include a means for testing the histocompatibility between the immature mammalian DC and a graft specimen.

In order to practice the present invention, it is not a requirement that the donor mammal and the host mammal be from the same species. For instance, immature DC from a baboon donor may be administered to a human host to facilitate tolerance-induction in the human host to a graft specimen from the baboon donor. This type of xenograft transplantation is described in, for example, Starzl, et al., Immunological Reviews, 141:213 (1994), the contents of which are herein incorporated by reference.

In an additional embodiment, the present invention also relates to a surgical transplant procedure for increasing graft acceptance in a host mammal comprising the steps:
 (a) administering to the host mammal immature mammalian DC isolated from a donor mammal, and
 (b) transplanting to the host mammal a graft specimen derived from the donor mammal.

The immature mammalian DC of this surgical transplant procedure may be administered in dosage unit form. Appropriate dosage unit forms, amounts and times of administration for the immature DC of the present invention are discussed hereinabove.

Xenograft transplants are encompassed by the inventors' surgical procedure.

In another embodiment, the present invention relates to a method for producing mature mammalian DC, whereby immature mammalian DC are cultured in the presence of a cytokine and an extracellular matrix protein. Immature mammalian DC of the present invention are preferably derived from an organ, and more preferably from a liver or bone marrow. Humans are the preferred source of immature mammalian DC. Examples of cytokines that may be used in the present invention, alone or in any combination, include, but are not limited to, GM-CSF, IL-1, IL-4 and TNF-α. GM-CSF is the preferred cytokine of the present invention. Examples of extracellular matrix proteins that may be employed in the present invention, alone or in any combination, include, but are not limited to, type-1 collagen, fibronectin and laminin. The preferred extracellular matrix protein of the present invention is collagen, and more preferably type-1 collagen.

In an additional embodiment, the present invention relates to a composition comprising immunologically mature mammalian DC. Features by which immunologically mature DC can be identified include an upregulated expression of MHC class II antigen, a reduction in phagocytic capacity and the acquisition of potent allostimulatory activity.

The mature mammalian DC of the present invention are cultured from immature mammalian DC in a culture containing a cytokine and an extracellular matrix protein. An example of the cell culturing techniques that can be employed to produce these immunologically mature mammalian DC from immature mammalian DC is detailed in the Examples section hereinbelow. Similar culturing techniques are also described in Lu, et al., J. Exp. Med., 179:1823–34 (1994), the contents of which are herein incorporated by reference. Additionally, those reasonably skilled in the art would appreciate modifications that could be made to the disclosed culturing techniques without engaging in undue experimentation.

The composition comprising immunologically mature mammalian DC is useful to enhance the immune response of a host mammal. This may be accomplished by administering the composition to a host mammal in an amount effective to enhance the immune response of the host mammal. Such enhancement is evidenced by the production of antibodies and cell-mediated immunity. The immune response of a host may be enhanced against an infectious agent, tumor, antigen requiring a potent immune response or the like.

In a further embodiment, the present invention relates to a kit for use in enhancing the immune response of a host mammal, which kit contains the immunologically mature mammalian DC of the above-described composition. The mature mammalian DC of this kit are preferably stored in a lyophilized form. The kit of the present invention may further contain a pharmaceutically acceptable carrier as described hereinabove.

In an additional embodiment, the present invention relates to a method of enhancing the immune response of a host mammal comprising the steps:
 (a) isolating immature mammalian DC from a donor mammal;
 (b) maturing said immature mammalian DC in the presence of a cytokine and an extracellular matrix protein; and
 (c) administering said mature mammalian DC to said host mammal in an amount effective to enhance the immune response of said host mammal.

The immature mammalian DC are preferably isolated and matured in accordance with the methods described hereinabove and in the Examples section hereinbelow. Efficacious dosages of the mature mammalian DC for enhancing the immune response of a host are believed to be similar to the dosages of immature mammalian DC discussed hereinabove for enhancing tolerogenicity in a host mammal to a graft specimen from a donor mammal.

The inventors' composition and method of enhancing immune response may also include the addition of one or more malignancy agents in dosage unit form. Examples of malignancy agents that can be used in the inventors' method of enhancing immune response include, but are not limited to, chemotherapeutics, anti-cancer vaccines and immune adjuvants, such as, for example, interleukin 12.

Those skilled in the art will possess sufficient knowledge to select an appropriate regimen of malignancy agents, whether used individually or in any combination, for administration to a patient exhibiting a particular set of indications. Examples of dosage unit forms contemplated by the present invention include capsule, tablet and emulsion for per os administration and a solution for intravenous, subcutaneous, intramuscular, intraperitoneal, intratumoral and peritumoral administration. Intravenous administration is preferred.

Means of administering the mature mammalian DC to their mammalian host include, but are not limited to, intravenous, subcutaneous, intraperitoneal, intratumoral and peritumoral. A pharmaceutically acceptable carrier, as described hereinabove, may be used with the mature mammalian DC of this method.

The following non-limiting examples illustrate the invention in more detail.

EXAMPLES

The following materials, methods and protocols were used in Examples 1 and 2 below.

Test Animals

Adult 8–12 week old male B10.BR (H-$2^k$, I-E$^+$) and C57BL/10SnJ (B10, H-$2^b$, I-E$^-$) mice were obtained from The Jackson Laboratory, Bar Harbor, Me., and maintained in a pathogen-free facility.

Isolation of Liver-Derived Non-Parenchymal Cells

Liver-derived NPC were isolated in accordance with the isolation protocol shown in FIG. 1. Before the liver-derived NPC were extracted, B10.BR mice were anaesthetized with metafen, swabbed in the abdominal region with 70% ethanol and an abdominal mid-line incision was performed. Livers of the B10.BR mice were then perfused for 3 min in situ via the inferior vena cava, using 30 ml Hank's balanced salt solution (HBSS; GIBCO BRL, Grand Island, N.Y.) and a 22G intravenous catheter (Critikon Inc., Tampa, Fla.). A 2 ml collagenase solution (Sigma, St. Louis, Mo.; 1 mg/ml of type-IV collagen in HBSS) was then injected via the portal vein into each liver. After the collagenase solution was injected, the liver was immediately excised, diced into small pieces and digested in a 20 ml collagenase solution (Sigma, St. Louis, Mo.; 1 mg/ml of type-IV collagen in HBSS) per liver for 30 min at 37° C., with constant stirring. The digested tissue was then filtered through a 0.1 mm sterile nylon mesh. The NPC from 2–4 livers were pooled.

The cell suspension was centrifuged at 400 g for 5 min and washed twice in RPMI-1640 (GIBCO BRL) supplemented with glutamine (2 mM/ml) (GIBCO BRL) non-essential amino acids (0.1 mM/ml) (GIBCO BRL), sodium pyruvate (1 mM/ml) (GIBCO BRL), 2-ME (20 $\mu$M) (GIBCO BRL) and antibiotics (GIBCO BRL; penicillin, 100 U/ml; GIBCO BRL; streptomycin, 100 mg/ml). After each wash in RPMI-1640, the cell suspension was centrifuged at 400 g for 5 min. The cells were resuspended in 7ml sterile, self-generating Percoll solution (Sigma; 1.130 relative density) and centrifuged at 4° C. for 10 min (39,000 g) using a SS34 rotor in a superspeed centrifuge (Sorvall RC-SB, DuPont Instruments, Chadds Ford, Pa.). The top layer of cells, which was comprised of intact hepatocytes and hepatocyte fragments, was removed and discarded. The cell suspension between the upper hepatocyte layer and the lower erythrocyte layer constituted the liver NPC population, which was harvested and washed twice in RPMI-1640 for 5 min each wash. Control spleen cell populations were also prepared in accordance with the above-described protocol.

Culturing of Liver or Spleen-Derived Cells in the Presence of GM-CSF

Liver NPC and spleen cells were cultured in the presence of GM-CSF by investing 2–5×$10^5$ liver NPC or spleen cells into each well of a 24-well plate containing 2 ml of RPMI-1640 (GIBCO BRL), supplemented with 10% FCS (Gibco BRL) and 0.4 ng/ml mouse recombinant GM-CSF (R&D Systems, Inc., Minneapolis, Minn.). The cultures were fed every other day by aspirating 50% of the supernatant after gentle swirling, and replenishing the culture with an equivalent volume of a fresh GM-CSF-supplemented medium, as described above. An objective of these washes was to remove non-adherent granulocytes, without dislodging clusters of developing DC that attached loosely to firmly-adherent macrophages. After 4 days of culturing, granulocytes were no longer significant contaminants of the cultures which were routinely maintained for 7–10 days.

In some experiments, in addition to GM-CSF, recombinant mouse INF-$\gamma$ (500 U/ml; Genzyme, Cambridge, Mass.) and/or recombinant human IFN-$\gamma$ (1000 U/ml; Collaborative Research, Bedford, Mass.) was also incorporated into the culture medium. Both non-adherent and adherent cells were characterized by Giemsa-staining.

Depletion of MHC Class II Positive (Ia$^+$) Cells

Cells released from growing clusters in 7 day GM-CSF-stimulated cultures of liver-derived cells were depleted of any Ia$^+$ cells by complement-dependent lysis. The cells harvested were washed in HBSS (3×5 min each) and resuspended at 2×$10^6$/ml in HBSS containing 12.5 $\mu$g/ml mouse anti-I-E$^k$ mAb (PharMingen, San Diego, Calif.). After incubation at 4° C. for 30 min, the cells were washed twice in HBSS resuspended in 1:8 low toxicity rabbit complement (Accurate Chemical & Scientific Corp.) and incubated for an additional 30 min at 37° C. before two final washes of 5 min each in HBSS were performed. After each wash, suspensions were centrifuged at 700 g for 5 min. The efficiency of Ia$^+$ cell depletion was confirmed both by immunocytochemical staining of cytospins and by flow cytometry.

Culturing of Putative Liver DC on Collagen-Coated Plates

Each well of a 24-well plate was coated with type-1 collagen (50 $\mu$g/ml) in 0.02N acetic acid (J. T. Baker, Phillipsburg, N.J.), purified from rat tail tendon (Collaborative Research Inc.) for 15 min at 37° C. The collagen solution was then decanted and the wells were allowed to air dry for 15 min at room temperature (RT) before washing twice in RPMI-1640 containing 10% FBS. Cells released from growing clusters in 6 or 7 day old GM-CSF-stimulated cultures, which were free of adherent cells and granulocytes, were transferred to the plates (7×$10^5$ cells/well) and maintained for an additional 3 days in the presence of GM-CSF (0.4 ng/ml) (R&D Systems). Spleen cells were similarly cultured. In some experiments, the cells were pre-treated to deplete all MHC class II$^+$cells in the manner discussed above.

Flow Cytometric Analysis

Liver or spleen cells (5×$10^5$/tube) in HBSS with 1% w/v (1%=1 g/100 ml) bovine serum albumin (BSA; Sigma) and 0.1% sodium azide (Sigma) were stained either by direct or indirect immunofluorescence. Details of the mAbs used are shown in Table 1. T-lymphocytes were identified using FITC-conjugated rat anti-mouse Thy 1.2, PE-conjugated rat anti-mouse CD4 or CD8-$\alpha$ or hamster anti-mouse CD3-$\epsilon$ (PharMingen). For the detection of B-cells, rat anti-mouse B220 (CD45RA; TIB146, ATCC) was used, followed by FITC-conjugated AffiniPure goat anti-rat IgG (Jackson Immunoresearch Labs. Inc., West Grove, Pa.). Anti-leukocyte common antigen (CD45, TIB122; ATCC, Rockville, Md.), anti-macrophage antibody (F4/80, HB198; ATCC), anti-heat stable antigen (J11D, TIB 183; ATCC) and antibodies directed against DC-restricted markers (33D1, TIB227; ATCC; NLDC-145, CD11c and N418; provided by Dr. R. M. Steinman, Rockefeller University, New York, N.Y.) were employed to further characterize the lineages of the isolated cells. The presence of natural killer ("NK") cells was revealed using antibodies against NK1.1 or LGL-1 (Dr. W. H. Chambers, Department of Pathology, University of Pittsburgh). The expression of accessory molecules was identified using antibodies against the IL-2 receptor (CD25, p55, PC61 5.3, TIB 222; ATCC), ICAM-1 (CD54; Serotec, Indianapolis, Ind.), Pgp-1 glycoprotein (CD44, TIB235; ATCC), CD11b (MAC-1$\alpha$ unit, M1/70, TIB 128; ATCC), and FcγRII (CD32; PharMingen). Appropriate FITC-conjugated anti-mouse, anti-rat or anti-hamster secondary antibodies were used. Normal hamster serum or the appropriate rat Ig isotypes were used as negative controls. Biotin-conjugated mouse anti-mouse I-E$^{k,d,p,r}$ (PharMingen) was used with FITC streptavidin (Jackson Immunoresearch Labs. Inc.) as the secondary reagent. Biotin-conjugated mouse IgG$_{2a}$ (Pharmingen), together with FITC streptavidin was used as a negative control. After staining, cells were fixed in 1% paraformaldehyde in saline before flow cytometric analysis was performed in a FACStar® flow cytometer (Becton Dickinson, San Jose, Calif.). Five thousand events were acquired for each sample. These results are recorded in FIGS. 2, 3, 5 and 6.

TABLE 1

Monoclonal Antibody Panel

| Antigen | Species/Isotype | Supplier/Clone Name (ATCC #) |
|---|---|---|
| Leukocyte Common Ag | | |
| CD45 | Rat IgG$_{2a}$ | M1/9.3.4 (TIB 122) |
| CD4SRA; B220 | Rat IgM | RA3-3A 1/6.1 (TIB 146) |
| MHC | | |
| Class II; I-E$^{k,d,p,r}$ | Mouse IgG$_{2a}$ | PharMingen; 14-4-4S (HB32) |
| DC-restricted | | |
| Lymphoid DC | Rat IgG$_{2b}$ | 33D1 (TIB 227) |
| Interdigitating Cell | Rat IgG$_{2a}$ | NLDC-145; Dr. R. M. Steinman |
| Myeloid (primarily) | | |
| Macrophage | Rat IgG$_{2b}$ | F4/80 (HB 198); Dr. R. M. Steinman |
| Lymphoid (primarily) | | |
| Thy 1.2 | Rat IgG$_{2a}$ | PharMingen; 53-2.1 |
| CD3-ε | Hamster IgG | PharMingen; 145-2C11 |
| CD4 | Rat IgG$_{2a}$ | PharMingen; RM-4-5 |
| CD8α | Rat IgG$_{2a}$ | PharMingen; 53-6.7 |
| Heat stable antigen | Rat IgM | J11D (TIB 183) |
| NK cells | | |
| NK 1.1 | Mouse IgG$_{2a}$ | Dr. W. H. Chambers |
| LGL-1 | Rat IgG$_{2a}$ | Dr. W. H. Chambers |
| Receptors/adhesions | | |
| CD32, FCγRII | Rat IgG$_{2b}$ | PharMingen; 2.4G2 (HB 197) |
| CD11b, MAC-1α unit; C3BiR | Rat IgG$_{2b}$ | M1/70. (TIB 128) |
| CD11c, p150/90 | Hamster IgG | N418; Dr. R. M. Steinman |
| CD44, Pgp-1 | Rat IgG$_{2a}$ | PharMingen; 2D2C (TIB 235) |
| CD54, ICAM-1 | Rat IgG$_{2a}$ | Serotec; KAT-1 |
| CD25, p55; IL-2R | Rat IgG$_1$ | PC 61 5.3 (TIB 222) |

Mixed Leukocyte Cultures

In order to test the immunogenicity of freshly-isolated or cultured cells, one-way mixed leukocyte cultures ($4\times10^5$ cells in 200 μl per well in 96-well, round-bottom microculture plates) were performed with γ-irradiated (20 Gy) allogeneic (B10.BR) or syngeneic (B10) liver NPC or spleen cells as stimulators. B10 spleen cells were used as responders, which were T-cell enriched by sequential removal of plastic-adherent cells (1 hour at 37° C.) and passage (1 hour) through a nylon wool column. Cultures were maintained in RPMI-1640 complete medium supplemented with 10% heat-inactivated FCS for 72 hours in 5% $CO_2$ in air. For the final 18 hours, 10μl[$^3$H]TdR (1 μCi) (New England Nuclear, Boston, Mass.) was added to each well. Cells were harvested onto glass fiber disks using a multiple cell harvester and the degree of thymidine incorporation was determined in a liquid scintillation counter. Results were expressed as mean counts per minute (cpm)±1SD.

Phagocytosis Assay

SRBC (Remel, Lenexa, Kans.) were washed extensively with ice-cold PBS and opsonized at 37° C. for 15 min with a sub-agglutinating concentration (1:100) of rabbit anti-SRBC IgG (Sigma). The washed SRBC were then suspended in RPMI-1640 and incubated at 37° C. for 2 hours (8:1) with freshly-harvested suspensions of GM-CSF-stimulated, non- and loosely-adherent liver-derived cells before and after exposure to collagen. Non-ingested SRBC were lysed in a hypotonic solution comprised of 75% RPMI-1640 and 25% $H_2O$ for 10 sec. The cells were then cytocentrifuged, fixed in methanol and stained with Giemsa. Phagocytic activity, as determined by the presence of at least 3 ingested SRBC, was evaluated "blind" by light microscopic examination. Overnight cultured peritoneal macrophages from the same mouse strain were used as positive controls.

Immunocytochemistry

The cytocentrifuge preparations were stained using avidin-biotin-peroxidase complex (ABC) staining procedures. The specimens were air dried at RT before fixing in acetone for 5 min. The slides were then washed in PBS and incubated for 1 hour at RT with biotinylated mouse IgG$_{2a}$ anti-mouse I-E$^{k,d,p,r}$ mAb. After three washes of 5 min each in PBS, the slides were incubated with streptavidin-biotin-peroxidase complex (ABC-P; Boehringer Mannheim Corp., Indianapolis, Ind.) for 30 min at RT and the color reaction was developed for 6 min using a peroxidase chromogen kit (AEC; Biomedia Corp., Foster City, Calif.). Cells were then counterstained lightly with hematoxylin. Controls either omitted antibody or used isotype-matched irrelevant mAb.

Dendritic Cell Homing

Ia-depleted or non-depleted cultured B10.BR liver or spleen cells were washed in RPMI-1640 and injected subcutaneously (1 or $2.5\times10^5$ cells in 50 μl) into one hind footpad or intravenously ($1\times10^6$ in 200 μl) via the lateral tail vein of normal B10 mice. One to 5 days later, the draining popliteal lymph node and spleen were removed and embedded in Tissue-Tek® (O.C.T. Compound; Miles Inc., Elkhart, Ind.). Sections of 10 μm were cut using a cryostat microtome at −30° C. and melted directly onto slides at RT. Slides were air-dried at RT overnight, and then stored at −70° C. until used. Just before staining, the slides were equilibrated at RT, then fixed in acetone before immunoperoxidase staining as described above. Tissue controls included sections of normal recipient strain (B10) tissues.

Ultrastructural Studies

Electron microscopy, both transmission and scanning, was performed using standard dehydration, embedment, sectioning, critical point drying and sputter coating techniques. Observation was with a 100CX transmission scanning electron microscope (JEOL T300; JEOL U.S.A., Peabody, Mass.).

EXAMPLE 1

Isolation of Liver-Derived NPC and Their Proliferation in Response to GM-CSF

Approximately $7-10\times10^6$ NPC were isolated per normal mouse liver, with less than 5% hepatocyte contamination by microscopic examination. A large proportion of the total cell population derived from both the liver and the spleen was B220$^+$ (B-cells) (approximately 40–50% in the liver and 60–80% in the spleen) as determined by flow cytometric analysis. These cells accounted in large measure for the MHC class II$^+$ (I-E$^+$) population of comparatively small-sized cells derived from each organ. Within the overall population of NPC, Thy1.2$^+$ T-cells were present in smaller numbers compared with B-cells (approximately 20% of the liver cell population and 30–40% of the spleen cell population). Interestingly, within the population of small-sized cells a distinct subpopulation of cells bearing the DC-restricted, interdigitating cell marker NLDC 145 was found in the liver, but not in the spleen. Gating for the more granular and larger-sized cells also revealed a much greater population of NLDC 145$^+$ cells amongst liver NPC as compared with spleen cells. The presence of these NLDC 145$^+$ cells represented the major phenotypic difference between splenocytes and liver NPC using the large panel of mAbs tested.

Liver NPC and spleen cells were separately cultured in the presence of GM-CSF. After 4 days of culturing, during which time non-adherent granulocytes were removed by gentle washes, the growth of cell "clusters" attached to a layer of adherent cells was observed. Moreover, many dendritic-shaped cells were apparently released from these clusters, exhibiting sheet-like cytoplasmic processes. When these liver and spleen cells were cultured in the presence of GM-CSF for an additional 2–6 days, these cells detached from the aggregates and many mononuclear cells with a typical dendritic shape were seen either loosely attached or floating in the culture medium. In the absence of GM-CSF, however, no cellular proliferation was seen.

Adherent macrophages and fibroblasts also expanded in the liver or spleen cell cultures in the presence of GM-CSF, but remained firmly attached to the plastic surface. The floating or loosely-adherent putative DC were harvested by gentle aspiration for further phenotypic or functional analyses. After 7 days of culturing in the presence of GM-CSF, approximately 2.5×10$^6$ of these cells per mouse liver could be harvested from the cultures.

Microscopic and Immunophenotypic Analysis of GM-CSF-Stimulated Liver and Spleen Cells At the microscopic level, the cells released from proliferating aggregates of GM-CSF-stimulated liver or spleen cells exhibited typical morphological features of DC, including (in many but not all cells) irregular-shaped eccentric nuclei, numerous "veil"-like cytoplasmic dendrites, abundant mitochondria and few electron-dense granules. Scanning electron microscopy provided further definitive evidence of gossamer-like "veils". To ascertain the surface phenotype of cells released from proliferating aggregates, flow cytometric analysis was performed after 6–10 days of culturing in the presence of GM-CSF, or even longer periods in some instances. Staining for cells of lymphoid lineage, including NK cells was absent.

As shown in FIG. 2A to 2F, the floating cells in the liver-derived cultures strongly expressed surface antigens that are known to be associated with mouse DC. These surface antigens included CD45 (leukocyte common antigen), heat stable antigen, ICAM-1, CD11b (MAC-1), and CD44 (non-polymeric determinant of Pgp.1 glycoprotein). In addition, staining of weak to moderate intensity was observed for the DC-restricted markers NLDC 145 (interdigitating cells), 33D1 and N418, F4/80 and for FcRII. The intensity of expression of these markers on GM-CSF-stimulated spleen cells was similar, except that 33D1 and NLDC 145 were slightly more and less intense, respectively, when compared with the liver-derived cells.

The inventors found that the liver-derived, GM-CSF-stimulated cells expressed only a low level of MHC class II (I-E$^k$) surface antigen molecule when compared to GM-CSF-stimulated spleen cells propagated under the same conditions (FIGS. 3A to 3D). The intensity of the I-E$^k$ expression could not be increased, on either the liver or spleen-derived cells, by increasing the concentration of GM-CSF (0.4–0.8 ng/ml) and/or by extending the culturing period up to 4 weeks. The low intensity of I-E$^k$ expression on the liver cell population suggested that these proliferating cells, though possessing several surface markers indicative of developing DC, were still at a phenotypically immature stage of differentiation. Other attempts to induce MHC class II antigen expression included combining GM-CSF with TNF-$\alpha$ (500 U/ml) and/or IFN-$\gamma$ (1000 U/ml) for up to 5 days and culturing on a "feeder layer" of irradiated, syngeneic spleen cells. None of these treatments affected the expression of cell surface I-E$^k$ on the putative "immature" liver DC to any significant degree.

Allostimulatory Activity by GM-CSF-Propagated Liver-Derived Cells

Figure 4:
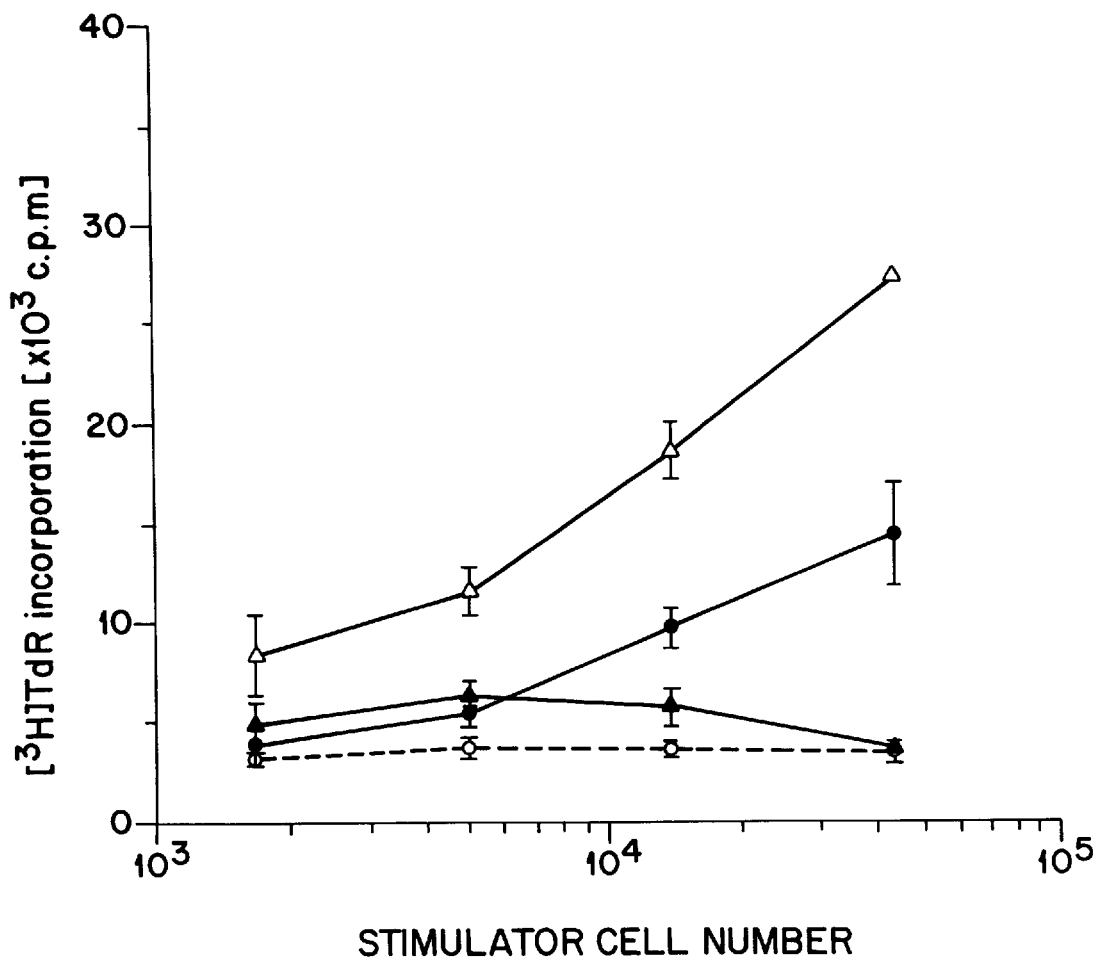
FIG. 4. This figure shows the allostimulatory activity of γ-irradiated, GM-CSF-stimulated B10.BR mouse liver putative DC [▲] or splenic DC [△], using naive B10 (I-E$^{31}$) splenic T-cells as responders. The non-adherent cells were harvested from 10 day GM-CSF-stimulated cultures and set up at various concentrations with 4×10$^5$ responder T-cells. Cultures were maintained for 72 hours and [$^3$H] TdR was added 18 hours before harvesting. The mixed leukocyte reaction-stimulatory ("MLR-stimulatory") activity of freshly isolated allogeneic (B.10 BR; [●]) and syngeneic (B10; [○]) spleen cells is also shown. The results are expressed as mean counts per minute (c.p.m.)±1SD and are representative of at least 3 separate experiments. Compared with the GM-CSF-stimulated spleen cells, the results indicate that the GM-CSF-liver derived cells failed to induce naive T-cell proliferation.

Because it was found that liver-derived cells propagated in the presence of GM-CSF demonstrate a relatively low cell surface expression of MHC class II antigen, the inventors investigated the allostimulatory activity of these cells. As a result, it was discovered that the GM-CSF cultured liver-derived cells do not induce naive T-cell proliferation (FIG. 4). In contradistinction, the GM-CSF-stimulated, spleen-derived DC, which express greater levels of surface MHC class II antigen, proved to be more efficient inducers of primary allogeneic T-cell responses than freshly isolated spleen cells. Furthermore, failure of the GM-CSF-stimulated putative liver DC to induce MLR contrasted with the potent allostimulatory activity of an overnight-cultured, non-adherent, low density mature DC enriched population that was prepared from freshly-isolated normal B10.BR mouse liver NPC, using conventional methods (Steinman, et al., J. Exp. Med., 137:1142 (1973); Steinman, et al., J. Exp. Med., 139:380 (1973))

Induction of MHC Class II on GM-CSF-Stimulated Liver-Derived Cells Following Exposure to Type-1 Collagen To overcome the obstacle to liver-derived DC maturation, the inventors discovered that if the putative "immature" liver DC were propagated in contact with type-1 collagen, an extracellular matrix protein that is expressed constitutively in the local microenvironment of the liver (located chiefly in portal triads, stroma of the portal spaces and around central veins), the liver-derived DC would mature. Immunochemistry was used to detect the maturation of the liver-derived DC (Hart, et al., J. Exp. Med., 154:347 (1981); Prickett, et al., Transplantation, 46:754(1988)).

Figure 5A:
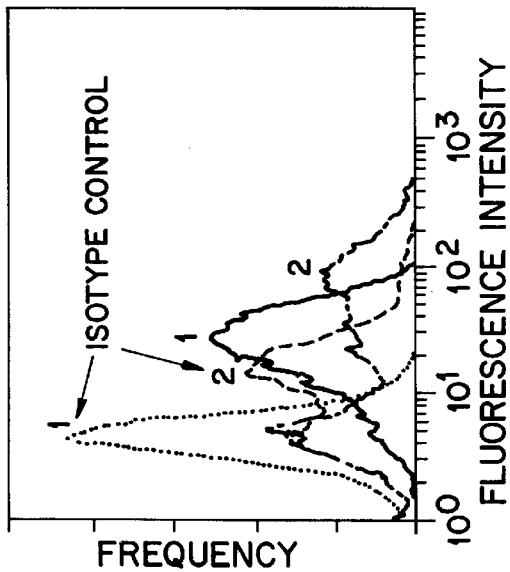
FIGS. 5A to 5D. These figures show an immunophenotypic analysis showing the expression of various DC-restricted markers (FIGS. 5A, 5C and 5D) and of F4/80 (FIG. 5B) on GM-CSF-stimulated putative liver DC before (1) and after (2) the exposure of the cells to type-1 collagen. Seven-day cultures of liver-derived cells released from aggregates in GM-CSF-supplemented medium were exposed for an additional 3 days to type-1 collagen or maintained without collagen in the continuous presence of GM-CSF (0.4 ng/ml). An isotype-matched irrelevant antibody was used as a negative control. The data represent the results of 3 separate experiments and clearly demonstrate a marked upregulation in the intensity of expression of the DC markers NLDC145 (FIG. 5C), 33D1 (FIG. 5A) and N418 (FIG. 5D).
Figure 5B:
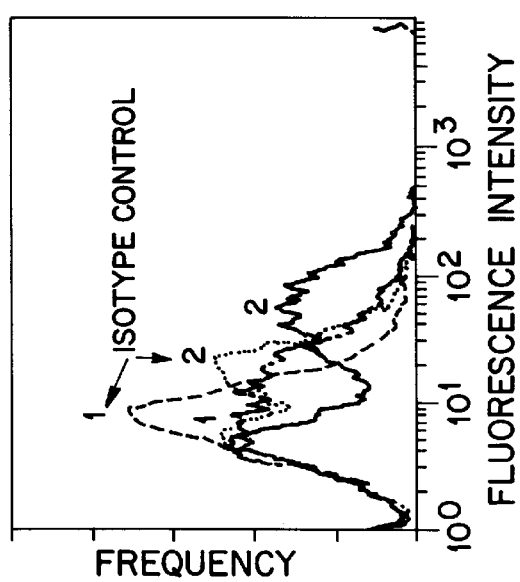
Figure 5C:
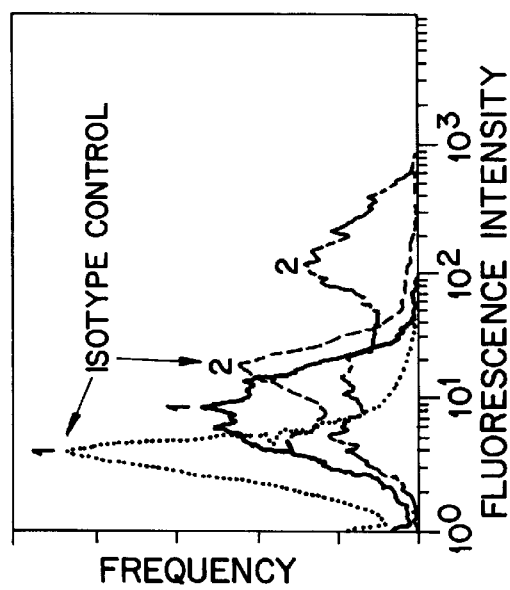
Figure 5D:
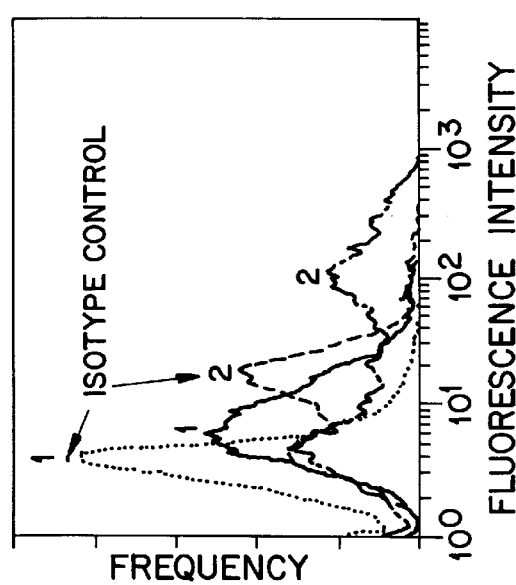

Seven day GM-CSF-stimulated liver cells expressing low levels of MHC class II antigen were transferred to culture plates pre-coated with type-1 collagen and maintained for 3 additional days in the presence of GM-CSF. Cell proliferation was observed on the collagen-coated plates, accompanied by a relative increase in non-adherent cells as compared with control cultures (collagen-free). Immunophenotypic analysis of the non-adherent cells showed marked upregulation in the intensity of expression of the DC markers NLDC145 (FIG. 5C), 33D1 (FIG. 5A) and N418 (FIG. 5D). Such upregulation of DC markers has been shown previously in GM-CSF-stimulated mouse bone marrow cultures (Inaba, et al., J. Exp. Med., 176:1693 (1992)). Of particular interest, however, was the inventors' observation that MHC class II antigen expression was markedly upregulated on liver-derived DC propagated for an additional 3 days on collagen-coated plates, as compared to similar cells maintained in collagen free cultures. This observation was confirmed by immunocytochemical staining of cytospins of these cells.

Figure 6:
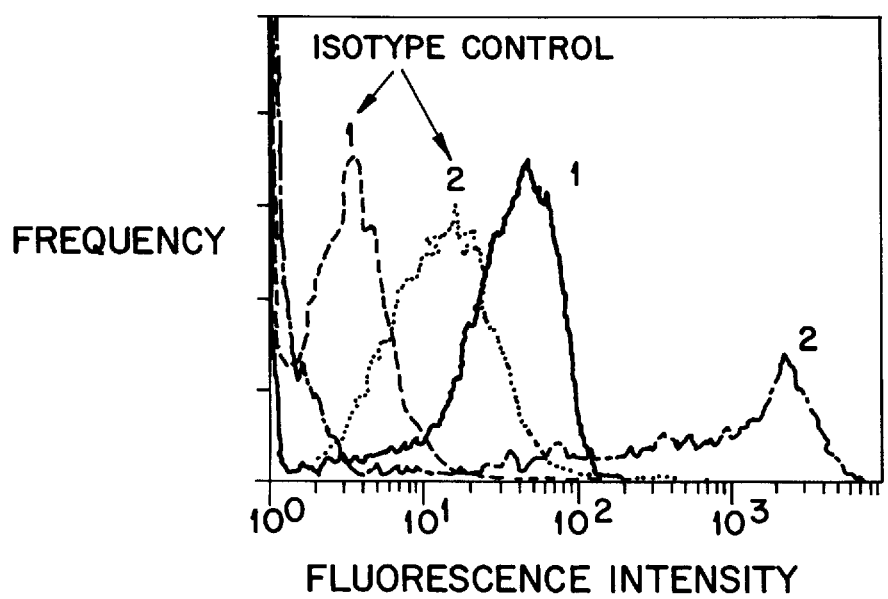
FIG. 6. This figure is the flow clytometric analysis of the expression of MHC class II (I-E$^k$) on GM-CSF-stimulated putative liver-derived DC without (1) or with (2) subsequent exposure to type-1 collagen. Ia$^+$(=MHC class II$^+$) cells were depleted from 7 day cultures of liver-derived cells released from aggregates in GM-CSF-supplemented medium by treatment with anti-Ia (I-E$^k$) mAb and complement. The cells were then exposed for an additional 3 days to type-1 collagen or maintained without collagen in the continuous presence of GM-CSF (0.4 ng/ml). An isotype-matched irrelevant antibody was used as a negative control. The data represent the results of 3 separate experiments and show that the Ia$^-$ population from these cells markedly upregulated its MHC class II expression when exposed to collagen for 3 days in the continued presence of GM-CSF.

The inventors recognized that the apparent upregulation of MHC class II antigen expression might actually be attributable to an enrichment of class $II^+$ cells. In order to discount this possibility, the inventors attempted to deplete the $Ia^+$ population by complement-mediated lysis prior to collagen exposure. Similar to the 7 day GM-CSF propagated liver-derived DC, the $Ia^-$ population obtained from these cells also markedly upregulated its MHC class II antigen expression when exposed to collagen for 3 days in the continued presence of GM-CSF (FIG. 6).

Cell proliferation was likewise observed when collagen-coated and collagen-free plates were compared. In each well of these plates, $1 \times 10^6$ $Ia^+$ cells were seeded and cultured in the presence of GM-CSF for 3 days. After culturing, $2 \times 10^6$ non-adherent cells were recovered from the collagen coated plates, whereas $1.5 \times 10^6$ non-adherent cells were recovered from the non-collagen-coated plates. The number of adherent cells was inversely related to the number of non-adherent cells recovered from the wells.

The above observations suggest that exposure of 7 day GM-CSF cultures of liver-derived DC to collagen does not lead to selective enrichment of $Ia^+$ cells, but rather reflect a phenotypic maturation, as evidenced by marked MHC class II upregulation. Furthermore, the intensity of this MHC class II antigen expression was similar to or greater than that observed on GM-CSF-stimulated spleen-derived DC (d10) which also expressed high levels of Ia, with or without exposure to an extracellular matrix protein. To control for possible trace contamination of the collagen with endotoxin and to rule out possible endotoxin-mediated upregulation of MHC class II antigen on the developing liver-derived DC, 7 day cultures were exposed to lipopolysaccharide (LPS) (50 pg/ml) for an additional 3 day period in the presence of GM-CSF. No increase in MHC class II expression was observed.

Reduction in Phagocytic Activity Following Exposure of Developing Liver-Derived DC to Type-1 Collagen Since one of the characteristic features of maturing DC is a progressive decrease in their phagocytic capacity, the inventors compared the ability of the developing, liver-derived DC to phagocytose opsonized SRBC before and after a 3 day exposure of the cells to type-1 collagen in the continued presence of GM-CSF. Following exposure to collagen, two separate experiments revealed a marked reduction in erythrophagocytic activity of the liver-derived DC, and a concomitant upregulation of MHC class II antigen.

Figure 7:
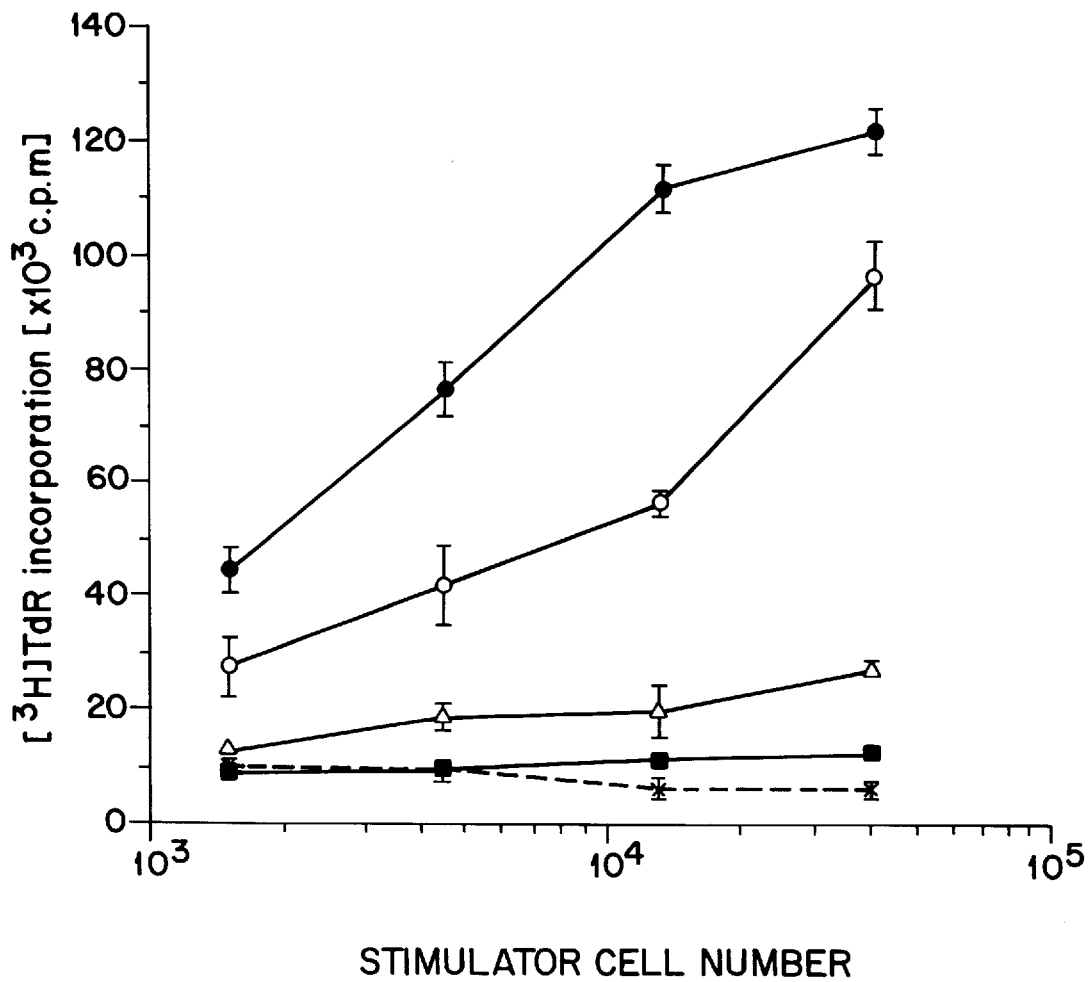
FIG. 7. This figure shows the allostimulatory activity of γ-irradiated, GM-CSF-stimulated B10.BR liver-derived DC from which all class II$^+$ cells were depleted with anti-Ia mAb and complement after 7 days of culturing. The cells were then exposed to type-1 collagen for 3 days. Ia-depleted stimulator cells that were maintained for 3 days with GM-CSF in collagen-free wells are represented by (■). Similarly-derived and treated cells, except for 3-day exposure to type-1 collagen in the continued presence of GM-CSF, are represented by (○). There was no increase in the MLR-stimulatory activity of untreated or Ia-depleted liver-derived cells maintained in GM-CSF alone for periods of more than 7 days, but not greater than 35 days. The allostimulatory activity of freshly-isolated (△) and GM-CSF-stimulated (after 10 days culturing) B10.BR spleen-derived DC (●), and syngeneic (B10) spleen cells (X) is also shown. The results are expressed as mean counts per minute+1SD and demonstrate that Ia-depleted liver-derived DC became potent inducers of MLR activity following exposure to collagen, in marked contrast to Ia-depleted cells maintained in GM-CSF alone, which failed to elicit T-cell proliferation.

Development of MLR Stimulatory Activity Following Exposure of Developing Liver-Derived DC to Type-1 Collagen The inventors next determined whether the collagen-induced upregulation of MHC class II expression on developing liver-derived DC was accompanied by a concomitant increase in their allostimulatory activity. Following exposure to collagen, Ia-depleted liver DC became potent inducers of MLR, in marked contrast to Ia-depleted cells maintained in GM-CSF alone, which failed to elicit T-cell proliferation (FIG. 7). These class $II^{bright}$ liver-derived DC also proved to be much stronger MLR stimulators than freshly-isolated spleen cells, although not as potent as GM-CSF stimulated splenocytes. This finding further strengthened the inventors' conclusion that the immature liver-derived DC had undergone maturation following 3 days of culturing in the continued presence of type-1 collagen and GM-CSF.

Homing of Liver-Derived DC

A specialized property of mature DC is their capacity to "home" to T-dependent areas of peripheral lymphoid tissues (Larsen, et al., J. Exp. Med., 171:307 (1990); Larsen, et al., J. Exp. Med., 172:1483 (1990)). To assess the homing ability of the developing liver-derived DC propagated in culture, 10 day GM-CSF-stimulated cells (1.0 or $2.5 \times 10^5$ low $I-E^k$ expression or $Ia^-$ following complement-mediated lysis, respectively) were injected subcutaneously into one hind footpad or intravenously into allogeneic B10 ($I-E^-$) recipients. For a comparative analysis, strongly class $II^+$ GM-CSF-stimulated spleen-derived DC (10 day cultures) were injected into separate animals. One to 5 days later, the animals were sacrificed and cryostat sections of the draining lymph nodes (where appropriate) and spleens were stained with donor-specific mAb to $I-E^k$. After injection, liver-derived cells propagated in GM-CSF-supplemented cultures homed almost exclusively to the T-cell areas of recipients' spleens in close proximity to arterioles. Similar observations were made in the draining lymph node of footpad-injected mice. (Thomson, et al., Transplantation, 59:1 (1995)).

Moderate to intense $I-E^k$ expression was detected on the liver-derived cells, many of which also exhibited distinct dendritic morphology. Five days after injection, liver-derived DC in the recipient's spleen were more abundant than strong class $II^+$ spleen-derived DC, which also homed after injection to T-cell areas of recipients' spleens and lymph nodes.

Similar observations were made regardless of whether $Ia^{dim}$ or Ia-depleted cells were injected. In the latter instance, however, the incidence of positive cells was reduced. These observations suggest that after injection, the immature liver-derived DC upregulate their MHC class II surface antigen in vivo. As previously shown for other non-lymphoid organ DC (Larsen, et al., J. Exp. Med., 171:307 (1990); Larsen, et al., J. Exp. Med., 172:1483 (1990)) maturing liver-derived DC propagated in the presence of GM-CSF and type-1 collagen exhibit the capacity to home to T-dependent areas of secondary lymphoid tissue and therein to express strong MHC class II cell surface antigen. This homing capacity is a key functional property of mature DC.

EXAMPLE 2

To determine whether GM-CSF stimulated, liver-derived immature mammalian DC exhibit tolerogenicity in vivo, the inventors tested murine recipients of allogeneic islet allografts in the following manner. Two days after rendering groups of 4 B10 ($H-2^b$; $I-A^+$) mice diabetic with streptozotocin (Sigma, St. Louis, Mo.) and 7 days before transplantation with 800 islets (99% pure) under the left renal capsule, the animals received intravenously either culture medium, $2.5 \times 10_6$ allogeneic (B10.BR; $H-2^k$ $I-E^+$) or syngeneic, 10-day cultured, GM-CSF stimulated liver DC progenitors or 10-day cultured, GM-CSF stimulated spleen DC.

By rendering the mice diabetic with streptozotocin, it was possible for the inventors to monitor the function of the transplanted, insulin-producing islet cells. The islet cell grafts operate to effectively rescue the animals from their induced-diabetic state. Conversely, the animals again become diabetic once the islet cell grafts are rejected.

Blood glucose and body weights of the animals were monitored daily. The graft survival times are shown in Table 2.

These results show that dendritic cell progenitors propagated in vitro have the capacity to enhance tolerogenicity of a host mammal to a transplanted graft specimen from a donor mammal. In particular, the data in Table 2 shows a prolongation of pancreatic islet allograft survival in 2 of the 4 animals given liver DC progenitors compared with untreated controls. Even longer survival rates would be expected with the administration of immunosuppressive agents. In addition, those skilled in the art would be able to modify the frequency of injections and number of DC injected to optimize the results of a specific application without requiring anything more than routine experimentation.

TABLE 2

| Donor   | Cells injected                                      | Islet graft survival (days) |
|---------|-----------------------------------------------------|-----------------------------|
| None    | (media control)                                     | 11, 12, 11, 11              |
| B10:    | GM-CSF stimulated liver DC progenitors (syngeneic)  | 15, 15, 17                  |
| B10.BR: | GM-CSF stimulated liver DC progenitors (allogeneic) | 29, 68, 61, 29              |
| B10.BR: | GM-CSF stimulated spleen DC (allogeneic)            | 11, 11, 15, 11              |

All references cited hereinabove are herein incorporated in their entirety by reference.

While the invention has been described in connection with what is presently considered to be the most practical and preferred embodiments, it is understood that the invention is not limited to the disclosed embodiments, but on the contrary is intended to cover various modifications and equivalent arrangements included within the spirit and scope of the appended claims.

Thus, it is to be understood that variations in the methods of propagating and inducing differentiation of immature mammalian dendritic cells, as well the compositions produced therefrom and uses thereof, can be made without departing from the novel aspects of the invention as defined in the claims.

What is claimed is:

1. A method for enhancing tolerance in a host mammal to an allogeneic donor graft comprising:
   (a) isolating immature mammalian dendritic cells from a donor mammal;
   (b) culturing said immature mammalian dendritic cells in an amount of a cytokine effective to produce dendritic cells which are characterized by either absence or weak expression of major histocompatibility complex class II antigen;
   (c) isolating said cultured dendritic cells; and
   (d) administering said cultured dendritic cells to the host mammal in an amount effective to enhance tolerance to said donor graft.

2. The method according to claim 1, wherein the immature mammalian dendritic cells are isolated from a source selected from the group consisting of an organ, tissue, bone marrow and blood.

3. The method according to claim 2, wherein the immature mammalian dendritic cells are isolated from an organ.

4. The method according to claim 3, wherein the organ is a liver.

5. The method according to claim 2, wherein the immature mammalian dendritic cells are isolated from bone marrow.

6. The method according to claim 1, wherein the immature mammalian dendritic cells are isolated from a human source.

7. The method according to claim 1, wherein the host mammal is human.

8. The method according to claim 1, wherein the cytokine is selected from the group consisting of granulocyte-macrophage colony stimulating factor, interleukin-1, and tumor necrosis factor-$\alpha$.

9. The method according to claim 8, wherein the cytokine is granulocyte-macrophage colony stimulating factor.

10. The method according to claim 1, further comprising administering one or more immunosuppressive pharmaceuticals in dosage unit form.

11. The method according to claim 1, further comprising administering a pharmaceutically acceptable carrier.

12. The method according to claim 1, wherein expression of major histocompatibility complex class II antigen by the administered dendritic cells occurs in T-dependent regions of secondary lymphoid tissue of the host mammal.

13. A surgical transplant procedure comprising the method of claim 1, and further comprising transplanting said donor graft to said host mammal.

14. The surgical transplant procedure according to claim 13, further comprising administering to the host mammal one or more immunosuppressive pharmaceuticals in dosage unit form.

15. The surgical transplant procedure according to claim 13, further comprising administering to the host mammal a pharmaceutically acceptable carrier.

16. The surgical transplant procedure according to claim 13, wherein the immature mammalian dendritic cells are isolated from a source selected from the group consisting of an organ, tissue, bone marrow and blood.

17. The surgical transplant procedure according to claim 16, wherein the immature mammalian dendritic cells are isolated from an organ.

18. The surgical transplant procedure according to claim 17, wherein the organ is a liver.

19. The surgical transplant procedure according to claim 16, wherein the immature mammalian dendritic cells are isolated from bone marrow.

20. The surgical transplant procedure according to claim 13, wherein the immature mammalian dendritic cells are isolated from a human source.

21. The surgical transplant procedure according to claim 13, wherein the host mammal is human.

22. The surgical transplant procedure according to claim 13, wherein expression of major histocompatibility complex class II antigen by the administered dendritic cells occurs in T-dependent regions of secondary lymphoid tissue of the host mammal.

23. The method according to claim 1, wherein said cultured dendritic cells do not express co-stimulatory molecules.

24. The method according to claim 13, wherein said cultured dendritic cells do not express co-stimulatory molecules.

25. A method for enhancing tolerance in a host mammal to an allogeneic donor graft comprising:
(a) isolating immature mammalian dendritic cells from a donor mammal;
(b) culturing said immature mammalian dendritic cells in an amount of a cytokine effective to produce dendritic cells which are characterized by either absence or weak expression of major histocompatibility complex class II antigen;
(c) isolating said cultured dendritic cells; and
(d) administering said cultured dendritic cells to the host mammal in an amount effective to enhance tolerance to said allogeneic donor graft, wherein said administered dendritic cells home to T-dependent areas of secondary lymphoid tissue in the host mammal.

26. The method according to claim 25, wherein said cultured dendritic cells do not express co-stimulatory molecules.

27. The method according to claim 25, wherein the immature mammalian dendritic cells are isolated from a source selected from the group consisting of an organ, tissue, bone marrow and blood.

28. The method according to claim 27, wherein the immature mammalian dendritic cells are isolated from an organ.

29. The method according to claim 28, wherein the organ is a liver.

30. The method according to claim 27, wherein the immature mammalian dendritic cells are isolated from bone marrow.

31. The method according to claim 25, wherein the immature mammalian dendritic cells are isolated from a human source.

32. The method according to claim 25, wherein the host mammal is human.

33. The method according to claim 25, wherein the cytokine is selected from the group consisting of granulocyte-macrophage colony stimulating factor, interleukin-1, and tumor necrosis factor-$\alpha$.

34. The method according to claim 33, wherein the cytokine is granulocyte-macrophage colony stimulating factor.

35. The method according to claim 25, further comprising administering one or more immunosuppressive pharmaceuticals in dosage unit form.

36. The method according to claim 25, further comprising administering a pharmaceutically acceptable carrier.

37. The method according to claim 25, wherein expression of major histocompatibility complex class II antigen by the administered dendritic cells occurs in T-dependent regions of secondary lymphoid tissue of the host mammal.

38. A surgical transplant procedure comprising the method of claim 25, and further comprising transplanting said allogeneic donor graft to said host mammal.

39. The method according to claim 38, wherein said cultured dendritic cells do not express co-stimulatory molecules.

40. The surgical transplant procedure according to claim 38, further comprising administering to the host mammal one or more immunosuppressive pharmaceuticals in dosage unit form.

41. The surgical transplant procedure according to claim 38, further comprising administering to the host mammal a pharmaceutically acceptable carrier.

42. The surgical transplant procedure according to claim 38, wherein the immature mammalian dendritic cells are isolated from a source selected from the group consisting of an organ, tissue, bone marrow and blood.

43. The surgical transplant procedure according to claim 42, wherein the immature mammalian dendritic cells are isolated from an organ.

44. The surgical transplant procedure according to claim 43, wherein the organ is a liver.

45. The surgical transplant procedure according to claim 42, wherein the immature mammalian dendritic cells are isolated from bone marrow.

46. The surgical transplant procedure according to claim 38, wherein the immature mammalian dendritic cells are isolated from a human source.

47. The surgical transplant procedure according to claim 38, wherein the host mammal is human.

48. The surgical transplant procedure according to claim 38, wherein expression of major histocompatibility complex class II antigen by the administered dendritic cells occurs in T-dependent regions of secondary lymphoid tissue of the host mammal.

49. The surgical transplant procedure according to claim 38, wherein the donor graft is a homograft.

50. The surgical transplant procedure according to claim 38, wherein dendritic cells are administered to the host mammal prior to transplantation of the donor graft.

51. The surgical transplant procedure according to claim 13, wherein dendritic cells are administered to the host mammal prior to transplantation of the donor graft.

52. A method for enhancing tolerance in a host mammal to an allogeneic donor graft comprising:
(a) isolating immature mammalian dendritic cells from a donor mammal;
(b) culturing said immature mammalian dendritic cells in an amount of a cytokine effective to produce dendritic cells which are characterized by either absence or weak expression of major histocompatability complex class II antigen, and either absence or weak expression of co-stimulatory molecules;
(c) isolating said cultured dendritic cells; and
(d) administering said cultured dendritic cells to the host mammal in an amount effective to enhance tolerance to said allogeneic donor graft, wherein said administered dendritic cells home to T-dependent areas of secondary lymphoid tissue in the host mammal.

53. The method according to claim 52, wherein the immature mammalian dendritic cells are isolated from a source selected from the group consisting of an organ, tissue, bone marrow and blood.

54. The method according to claim 53, wherein the immature mammalian dendritic cells are isolated from an organ.

55. The method according to claim 54, wherein the organ is a liver.

56. The method according to claim 53, wherein the immature mammalian dendritic cells are isolated from bone marrow.

57. The method according to claim 52, wherein the immature mammalian dendritic cells are isolated from a human source.

58. The method according to claim 52, wherein the host mammal is human.

59. The method according to claim 52, wherein the cytokine is selected from the group consisting of granulocyte-macrophage colony stimulating factor, interleukin-1, and tumor necrosis factor-$\alpha$.

60. The method according to claim 59, wherein the cytokine is granulocyte-macrophage colony stimulating factor.

61. The method according to claim 52 further comprising administering one or more immunosuppressive pharmaceuticals in dosage unit form.

62. The method according to claim 52, further comprising administering a pharmaceutically acceptable carrier.

63. The method according to claim 52, wherein expression of major histocompatibility complex class II antigen by the administered dendritic cells occurs in T-dependent regions of secondary lymphoid tissue of the host mammal.

64. A surgical transplant procedure comprising the method of claim 52, and further comprising transplanting said donor allogeneic graft to said host mammal.

65. The surgical transplant procedure according to claim 64, further comprising administering to the host mammal one or more immunosuppressive pharmaceuticals in dosage unit form.

66. The surgical transplant procedure according to claim 64, further comprising administering to the host mammal a pharmaceutically acceptable carrier.

67. The surgical transplant procedure according to claim 64, wherein the immature mammalian dendritic cells are isolated from a source selected from the group consisting of an organ, tissue, bone marrow and blood.

68. The surgical transplant procedure according to claim 67, wherein the immature mammalian dendritic cells are isolated from an organ.

69. The surgical transplant procedure according to claim 68, wherein the organ is a liver.

70. The surgical transplant procedure according to claim 67, wherein the immature mammalian dendritic cells are isolated from bone marrow.

71. The surgical transplant procedure according to claim 64, wherein the immature mammalian dendritic cells are isolated from a human source.

72. The surgical transplant procedure according to claim 64, wherein the host mammal is human.

73. The surgical transplant procedure according to claim 64, wherein expression of major histocompatibility complex class II antigen by the administered dendritic cells occurs in T-dependent regions of secondary lymphoid tissue of the host mammal.

74. The surgical transplant procedure according to claim 64, wherein the donor graft is a homograft.

75. The surgical transplant procedure according to claim 64, wherein dendritic cells are administered to the host mammal prior to transplantation of the donor graft.

* * * * *